(12) United States Patent
Schmidt et al.

(10) Patent No.: US 6,872,362 B2
(45) Date of Patent: Mar. 29, 2005

(54) VIAL HANDLING SYSTEM WITH IMPROVED MIXING MECHANISM

(75) Inventors: Harry W. Schmidt, Fairfield, OH (US); David M. Neal, Hamilton, OH (US); Anthony B. Morris, Dayton, OH (US)

(73) Assignee: Teledyne Tekmar Company, Mason, OH (US)

(*) Notice: Subject to any disclaimer, the term of this patent is extended or adjusted under 35 U.S.C. 154(b) by 853 days.

(21) Appl. No.: 09/803,405

(22) Filed: Mar. 9, 2001

(65) Prior Publication Data
US 2001/0024624 A1 Sep. 27, 2001

Related U.S. Application Data
(60) Provisional application No. 60/188,665, filed on Mar. 11, 2000, and provisional application No. 60/188,269, filed on Mar. 10, 2000.

(51) Int. Cl.[7] .................................................. B01L 9/00
(52) U.S. Cl. ........................................ 422/104; 422/63
(58) Field of Search ............................ 422/104, 63, 64, 422/65, 100

(56) References Cited

U.S. PATENT DOCUMENTS

| | | | | |
|---|---|---|---|---|
| 2,350,534 A | * | 6/1944 | Rosinger | 366/274 |
| 2,518,758 A | * | 8/1950 | Cook | 366/274 |
| 3,028,476 A | * | 4/1962 | Hug | 219/443.1 |
| 3,138,370 A | * | 6/1964 | Anderson et al. | 366/274 |
| 3,211,433 A | * | 10/1965 | Chrostowski et al. | 366/274 |
| 3,333,829 A | * | 8/1967 | Moore et al. | 366/145 |
| 3,384,353 A | * | 5/1968 | Worth | 366/274 |
| 3,489,521 A | * | 1/1970 | Buckle et al. | 422/65 |
| 3,514,081 A | * | 5/1970 | Cavanaugh et al. | 366/342 |
| 3,521,715 A | | 7/1970 | Krutein | |
| 3,758,274 A | * | 9/1973 | Ritchie et al. | 422/50 |
| 4,038,875 A | | 8/1977 | Walkotten | |
| 4,310,057 A | | 1/1982 | Brame | |
| 5,227,139 A | | 7/1993 | Wong | |
| 5,472,559 A | * | 12/1995 | Cayford et al. | 156/554 |
| 5,473,437 A | * | 12/1995 | Blumenfeld et al. | 356/417 |
| 5,945,070 A | | 8/1999 | Kath et al. | |
| 5,948,360 A | * | 9/1999 | Rao et al. | 422/65 |
| 6,042,787 A | | 3/2000 | Pawliszyn | |
| 6,180,410 B1 | | 1/2001 | Gerstel et al. | |
| 6,447,728 B1 | | 9/2002 | Wilmes et al. | |
| 2002/0094304 A1 | | 7/2002 | Yang et al. | |
| 2002/0168778 A1 | | 11/2002 | Andrien, Jr. et al. | |
| 2003/0003596 A1 | | 1/2003 | Pawliszyn | |

OTHER PUBLICATIONS

U.S. Appl. No. 09/803,407, filed Mar. 9, 2001.
U.S. Appl. No. 09/803,412, filed Mar. 9, 2001.
U.S. Appl. No. 09/803,414, filed Mar. 9, 2001.
U.S. Appl. No. 09/803,721, filed Mar. 9, 2001.

* cited by examiner

Primary Examiner—M. Alexandra Elve
(74) Attorney, Agent, or Firm—Kirkpatrick & Lockhart Nicholson Graham LLP

(57) ABSTRACT

A vial autosampler includes a vial cup adapted to contain a vial with a stir member inside. The vial autosampler includes a vial mixing system for agitating the contents of the vial. The mixing system has an actuator, such as a motor, and a mixing hub that is coupled to the actuator. The mixing hub includes at least one magnetic field source disposed to rotate a magnetic field about the vial cup.

18 Claims, 2 Drawing Sheets

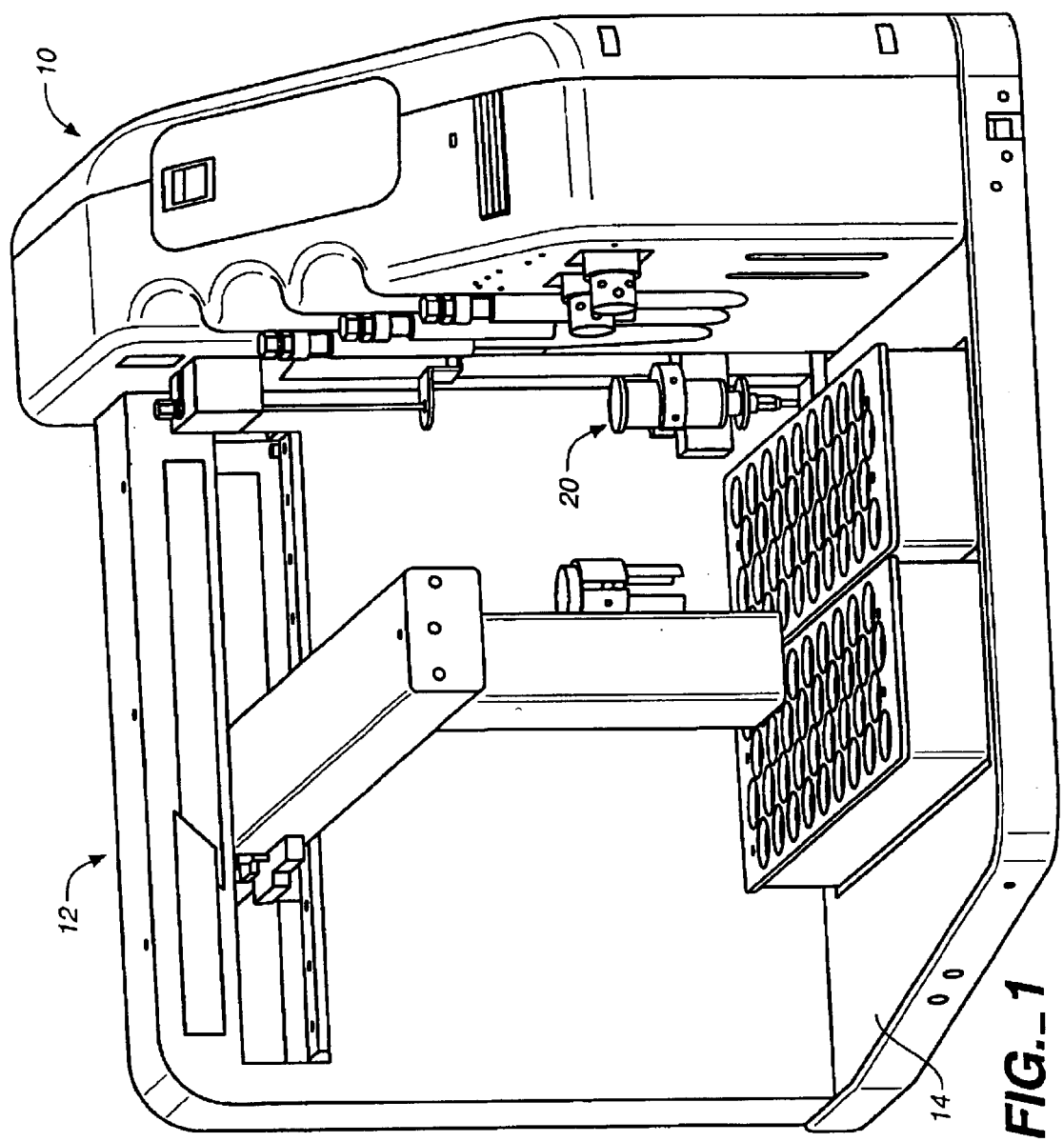
FIG._1

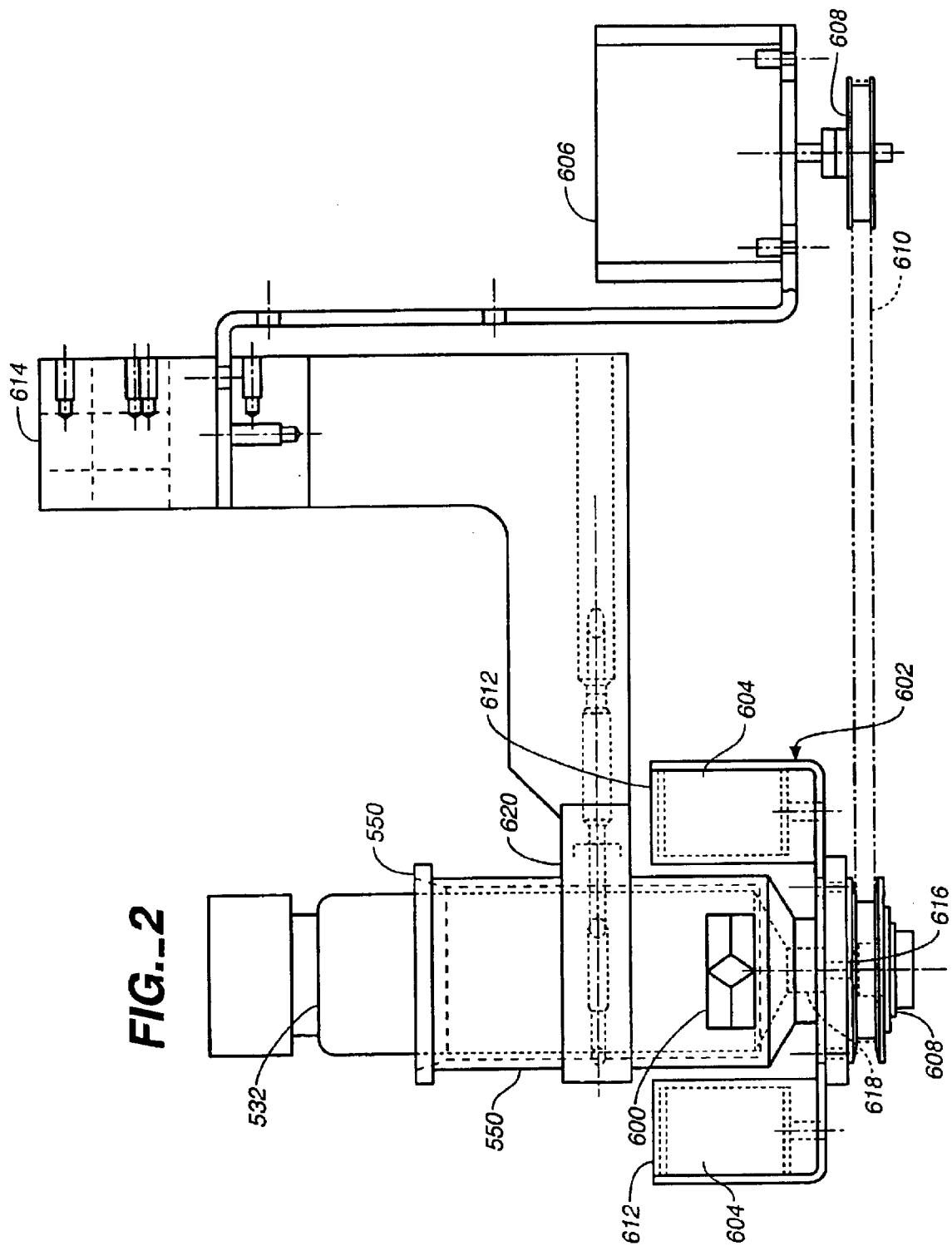

VIAL HANDLING SYSTEM WITH IMPROVED MIXING MECHANISM

CROSS REFERENCE TO RELATED APPLICATIONS

This application claims the priority of earlier filed co-pending provisional patent application Ser. Nos. 60/188,665, filed Mar. 11, 2000 and entitled IMPROVED VIAL HANDLING SYSTEM; and 60/188,269 filed Mar. 10, 2000 and entitled WATER AND SOIL AUTOSAMPLER.

BACKGROUND OF THE INVENTION

The present invention relates to vial autosamplers of the type used for laboratory automation. More specifically, the present invention relates to sample mixing within the vial autosampler.

Vial autosamplers are used to automate laboratory analyses associated with gas chromatography, carbon measurement (total carbon and total organic carbon) as well as other types of analyses. Typically, a vial autosampler has a storage area adapted to hold a number of vials to be analyzed. A robotic system generally grasps one of the vials and transports it from the storage area to an analytical site. Once transported to the analytical site, the vial contents are sampled and the appropriate analysis is performed.

Autosamplers typically use separate sampling modules for extracting liquid and gas samples. One example of such an autosampler is described in U.S. Pat. No. 5,948,360 to Rao et al. and assigned to Tekmar Company of Cincinnati, Ohio. Liquid sampling typically involves extracting a known quantity of liquid from the vial that is presented to the sampling module of the autosampler, adding a standard to the sample, and transferring the sample to an analytical device. Under certain situations, the specimen must be diluted by a technician by injecting the specimen with a specified volume of methanol or a water-based solution prior to sampling. The extracted sample or methanol extract is then diluted with water prior to analysis by the analytical device.

Gas headspace extraction generally involves injecting the specimen with a solvent, such as water, agitating the specimen, and purging the specimen with a gas. Some autosamplers are adapted to perform static headspace extraction while others are adapted to perform dynamic headspace extraction. In static headspace extraction, the specimen is purged from above the specimen and the headspace is removed and transferred to the analytical device. In dynamic headspace extraction, the specimen is purged from underneath the specimen and the head space is removed and then transferred to the analytical instrument. Autosamplers that are capable of performing the above sample extraction include the Precept II and the 7000 HT autosamplers sold by Tekmar-Dohrmann, of Cincinnati, Ohio.

When sample agitation is desired, a stir member, such as a stir bar is generally provided within the vial. The stir member is designed to interact with magnetic fields. Then, a mixing mechanism subjects the stir member to varying magnetic fields. This is typically done by spinning a magnet either beside the vial, or under the vial. In these instances the magnetic field is simply varying, while remaining essentially stationary. This technique is limited in that the strength of magnetic coupling is not optimal. Thus, in samples where agitation may be a challenge, such as soil samples, the mixing mechanism may fail to generate rotation of the stir member, thus reducing the solvent's effects within the sample.

As sample analysis becomes more and more precise, quantifying concentration down into the parts-per-trillion, it becomes increasingly important to provide very effective sample agitation. A more effective mixing mechanism would indeed provide more effective analysis, while possibly reducing cycle times.

SUMMARY OF THE INVENTION

A vial autosampler includes a vial cup adapted to contain a vial with a stir member inside. The vial autosampler includes a vial mixing system for agitating the contents of the vial. The mixing system has an actuator, such as a motor, and a mixing hub that is coupled to the actuator. The mixing hub includes at least one magnetic field source disposed to rotate a magnetic field about the vial cup.

BRIEF DESCRIPTION OF THE DRAWINGS

FIG. 1 is a perspective view of an illustrative automatic vial handling system with which embodiments of the present invention are useful.

FIG. 2 illustrates a mixing system for vial autosamplers.

DETAILED DESCRIPTION OF THE PREFERRED EMBODIMENTS

FIG. 1 shows a perspective view of a vial autosampler device 10 in accordance with the invention. The device 10 includes a base unit 12 that includes a vial storage platform area 14, a sampling station 20, and a fluid handling system comprising valves, glasswork, an other fluid handling components. Sampling station 20 receives a vial containing a specimen and extracts a fluid from the vial for further analysis. Finally, device 10 includes a central programmable control circuit that accepts user inputs and controls the operation of device 10.

In operation, a vial is selected from vial storage are 14 and transported to an analytical site. The vial is generally positioned within a vial cup in the sampling module, which lifts the vial such that a resilient septum, generally on top of the vial, is pierced by a stationary needle. In order to obtain the sample, a solvent may be introduced in the vial, and the contents agitated by a mixing mechanism. Once the vial has been sufficiently agitated, the sample is obtained. In some cases, a purge gas is bubbled through the solvent/sample mixture thereby entraining analytes. The purge gas with entrained analytes is recovered and analyzed in accordance with any suitable technique.

FIG. 2 illustrates a mixing system that is useful with vial autosamplers. One particular example of an analysis employing agitation is the analysis of soil. More specifically, EPA (Environmental Protection Agency) test method 5035, requires the addition of a stir member or stir member to a 40 milliliter vial for soil analysis. The stir member is magnetically coupled to an external agitator such that it rotates, or otherwise agitates the content of the vial.

FIG. 2 illustrates vial 532 resting within vial cup 550, and containing stir member 600. Stir member 600 can be any known stir member of suitable geometry, or any other device suitably able to magnetically couple to magnetic fields. Typically, stir members have a magnetic core which is coated with a chemically inert material such as polytetrafluoroethylene (PTFE) such as Teflon®, available from DuPont. However, as will be described later in the specification the magnetic coupling provided by the apparatus shown in FIG. 2 is generally stronger than that of previous stirring mechanisms. This is because systems that spin a magnet beside the vial have positions where the magnetic poles of the external magnet and the stir member are not aligned. Moreover, in systems where the magnet spins beneath the vial, the poles of the external magnet and the stir member are generally not as close to each other as systems that provide the magnet beside the vial. Due to the enhanced magnetic coupling of embodiments of the present invention, stir members with metal cores can also be used. Such stir members may in fact be easier to produce and have lower costs than magnetic-core stir members. Such cost savings are significant for test methods where stir rods are added to each and every vial, such as tests in accordance with EPA test 5035.

Mixing hub 602 is rotatably mounted beneath vial cup 550 and includes one or more magnets 604. Mixing hub 602 is generally rotated by an actuator such as a motor, or the like, such that magnets 604 rotate about vial cup 550. In the embodiment shown in FIG. 2, two magnets 604 are shown and mixing hub 602 is driven by stepper motor 606 which is coupled to mixing hub 602 through pulleys 608 and belt 610. Those skilled in the art will recognize that a number of methods can be used to rotate mixing hub 602 including chain drives, gear drives, direct coupling, and other suitable methods. All such methods are expressly contemplated. Magnets 604 are preferably held within mixing hub 602 by end caps 612. By providing one or more magnets which rotate about vial cup 550, the magnetic field is rotated about the vial, unlike prior art approaches where the field source is relatively stationary and simply spins. Even in embodiments where one magnet is used, stirring member 600 will be drawn to that magnet and essentially pulled around the inner diameter of vial 532. Additionally, when two magnets 604 are used, magnets 604 couple to individual magnetic poles of stir member 600 thus creating a stronger magnetic coupling than previous stirring systems. The enhanced magnetic coupling allows stir member 600 to stir the contents of vial 532 in applications when traditional stir systems would prove ineffective.

Another advantage of the stir system shown in FIG. 2, is that it is possible to continuously stir the contents of vial 532 even as elevator 614 causes vial cup 550 to lift vial 532. Such in transit mixing reduces the amount of time that a vial must sit at a mixing station, thus reducing the total analytic time for vial 532 and thereby increasing total system throughput. Additionally, it can be advantageous to cause elevator 614 to move mixing 602 up and down during mixing thereby causing both agitation in the vertical axis as well.

In one embodiment, motor 606 receives energization commands such that the instantaneous rotational speed of mixing hub 602 is varied as a function of the angular position thereof. For example, if the maximum rotational speed is M, and the instantaneous angular position of mixing hub 602 is $\theta$, then the instantaneous rotational speed, i, is related to $M \sin(\theta)$. Although the $\sin(\ )$ function is preferred for profiled mixing, a number of other mathematical functions can be used.

Another feature of the mixing system shown in FIG. 2 is that passageway 616 of hub 602 aligns with hole 618 in the bottom of vial cup 550. Thus, the combination of passageway 616 and hole 618 facilitate needle rinsing when vial 532 is not present since the needle can eject rinse fluid into vial cup 550 which drains out the bottom of passageway 616.

In vial autosamplers with a single analytical site for both solid and liquid containing vials, it is often necessary to change vial temperature during various stages during the analysis. One challenge, however, is that once vial cup 550 is heated, it may be necessary to wait for vial cup 550, and the vial held within, to cool to a selected temperature before further analysis can be performed. Thus, it is advantageous to provide features which facilitate the cooling of vial cup 550. To that effect, mixing hub 602 is preferably configured to enhance airflow around vial cup 550 when mixing hub 602 rotates. For example, the shapes of magnets 604 can be selected to be relatively thin rectangles thus providing significant surface area to cause airflow around vial cup 550. Further, fins or vanes can also be provided on mixing hub 602 to increase airflow further. In order to enhance cooling even further, thermoelectric devices, such as Peltier devices, can be mounted on vial cup 550 to thermoelectrically cool vial cup 550. Further still, magnets 604 and the additional fins can be configured to provide airflow around the Peltier devices to further enhance cooling of vial cup 550.

Although the present invention has been described with reference to preferred embodiments, workers skilled in the art will recognize that changes may be made in form and detail without departing from the spirit and scope of the invention. For example, although the mixing system is described with respect to permanent magnets rotating about the vial cup, it is expressly contemplated that electromagnets could be located about the vial at different angular position and successively energized in such a way that the magnetic field(s) rotate(s) about the vial cup without actually requiring physical movement.

What is claimed is:

1. In a vial auto sampler having a vial cup adapted to contain a vial having a stir member therein, a vial mixing system comprising:
   an actuator; and
   a mixing hub operably coupled to the actuator and having at least one magnetic field source disposed to rotate a magnetic field about the vial cup at a rotational speed that varies as a function of angular position.

2. The system of claim 1, wherein the actuator is a rotary motor.

3. The system of claim 2, wherein the actuator is coupled to the hub by a belt.

4. The system of claim 1, wherein the at least one magnetic field source rotates about the vial.

5. The system of claim 1, wherein the at least one magnetic field source comprises a pair of magnets.

6. The system of claim 1, wherein the at least one magnetic field source comprises a rectangular magnet.

7. The system of claim 1, and further comprising at least one fin mounted to the mixing hub to generate airflow with respect to the vial cup during rotation.

8. The system of claim 1, and further comprising a thermoelectric device couplable to the vial cup.

9. The system of claim 1, wherein the at least one magnetic source consists of a single magnet.

10. The system of claim 1, wherein the hub includes a central passageway to permit needle rinsing.

11. A method of mixing a sample in a vial, the method comprising:
   providing a stir member within the vial that is affectable by a magnetic field;
   generating a magnetic field proximate the stir member; and
   rotating the magnetic field about the vial at a rotational speed that varies as a function of angular position.

12. The method of claim 11, wherein the rotational speed is varied as a periodic function of angular position.

13. The method of claim 12, wherein the periodic function is a sine function.

14. The method of claim 11 and further comprising generating airflow around the vial.

15. The method of claim 11, wherein rotating the magnetic field about the vial includes rotating a magnetic source about the vial.

16. The method of claim 11, and further comprising:
raising the vial while the magnetic field rotates about the vial.

17. The method of claim 11, and further comprising:
lowering the vial while the magnetic field rotates about the vial.

18. A vial autosampler comprising:
means for storing vials;
means for moving vials from the means for storing vials to a means for analyzing samples; and
means for rotating a magnetic field about at least one of the vials at a rotational speed that varies as a function of angular position.

* * * * *